United States Patent
Abe et al.

(10) Patent No.: US 8,512,897 B2
(45) Date of Patent: Aug. 20, 2013

(54) PHENYL SULFONATE COMPOUND, NONAQUEOUS ELECTROLYTE SOLUTION USING THE SAME, AND LITHIUM BATTERY

(75) Inventors: Koji Abe, Yamaguchi (JP); Kazuhiro Miyoshi, Yamaguchi (JP)

(73) Assignee: Ube Industries, Ltd., Ube-shi (JP)

( * ) Notice: Subject to any disclaimer, the term of this patent is extended or adjusted under 35 U.S.C. 154(b) by 483 days.

(21) Appl. No.: 12/740,122

(22) PCT Filed: Oct. 24, 2008

(86) PCT No.: PCT/JP2008/069301
§ 371 (c)(1),
(2), (4) Date: Jul. 27, 2010

(87) PCT Pub. No.: WO2009/057515
PCT Pub. Date: May 7, 2009

(65) Prior Publication Data
US 2010/0291437 A1    Nov. 18, 2010

(30) Foreign Application Priority Data
Nov. 1, 2007    (JP) .................... 2007-285074

(51) Int. Cl.
*H01M 6/14*    (2006.01)

(52) U.S. Cl.
USPC ........... 429/199; 429/200; 429/307; 429/336; 429/340; 429/330; 429/332; 252/62.2; 568/35

(58) Field of Classification Search
USPC ................. 429/199, 200, 307, 336, 340, 330, 429/332; 252/62.2; 568/35
See application file for complete search history.

(56) References Cited

U.S. PATENT DOCUMENTS

| | | | |
|---|---|---|---|
| 6,303,816 B1 | 10/2001 | Arnold et al. | |
| 2005/0255384 A1 | 11/2005 | Abe et al. | |

(Continued)

FOREIGN PATENT DOCUMENTS

| CN | 1251523 A | 4/2000 |
|---|---|---|
| CN | 1864299 A | 11/2006 |

(Continued)

OTHER PUBLICATIONS

Chinese Office Action Issued Jul. 17, 2012 in Patent Application No. 200880113625.1.
U.S. Appl. No. 13/003,920, filed Jan. 13, 2011, Abe.
Nishihara, Y. et al., "Coupling Reactions of Alkynylsilanes Mediated by a Cu (I) Salt: Novel Syntheses of Conjugate Diynes and Disubstituted Ethynes", Journal of Organic Chemistry, vol. 65, No. 6, pp. 1780-1787 (2000).

(Continued)

*Primary Examiner* — Laura Weiner
(74) *Attorney, Agent, or Firm* — Oblon, Spivak, McClelland, Maier & Neustadt, L.L.P.

(57) ABSTRACT

Provided are (1) a novel phenyl sulfonate compound, (2) a nonaqueous electrolytic solution comprising an electrolyte salt dissolved in a nonaqueous solvent and containing a phenyl sulfonate compound of the following general formula (II) in an amount of from 0.01 to 10% by mass of the nonaqueous electrolytic solution, and (3) a lithium battery containing the nonaqueous electrolytic solution and excellent in low-temperature cycle property.

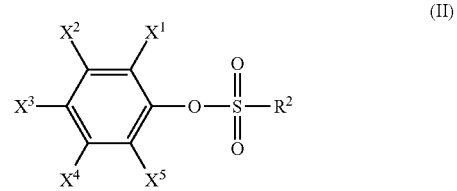

(wherein $X^1$ to $X^5$ each independently represents a fluorine atom or a hydrogen atom, and from one to four of these are fluorine atoms; $R^2$ represents a linear or branched alkyl group having from 1 to 6 carbon atoms, a linear or branched alkyl group having from 1 to 6 carbon atoms in which at least one hydrogen atom is substituted with a halogen atom, or an aryl group having from 6 to 9 carbon atoms).

25 Claims, 1 Drawing Sheet

(56) References Cited

U.S. PATENT DOCUMENTS

| | | |
|---|---|---|
| 2007/0054185 A1 | 3/2007 | Abe et al. |
| 2007/0172730 A1 | 7/2007 | Iwanaga et al. |

FOREIGN PATENT DOCUMENTS

| | | |
|---|---|---|
| JP | 2001 511781 | 8/2001 |
| JP | 2003 272700 | 9/2003 |
| JP | 2007 200688 | 8/2007 |
| WO | 2005 029631 | 3/2005 |
| WO | 2006 077763 | 7/2006 |
| WO | WO 2006/069788 A1 | 7/2006 |

OTHER PUBLICATIONS

Frohn, H.-J. et al., "A Simple and Convenient Route to Arylxenon (II) Tetrafluoroborates", Zeitschrift Fuer Naturforschung, B: Chemical Sciences, vol. 54, No. 12, pp. 1495-1498 (Dec. 1999).

Dolle, R. E. et al., "Palladium Catalyzed Alkoxycarbonylation of Phenols to Benzoate Esters", Journal of the Chemical Society, Chemical Communications, No. 12, pp. 904-905 (Jun. 15, 1987).

Hay, L. A. et al., "Palladium-Catalyzed Hydroarylation of Propiolamides. A Regio-and Stereocontrolled Method for Preparing 3, 3-Diarylacrylamides", Journal of Organic Chemistry, vol. 63, No. 15, pp. 5050-5058 (1998).

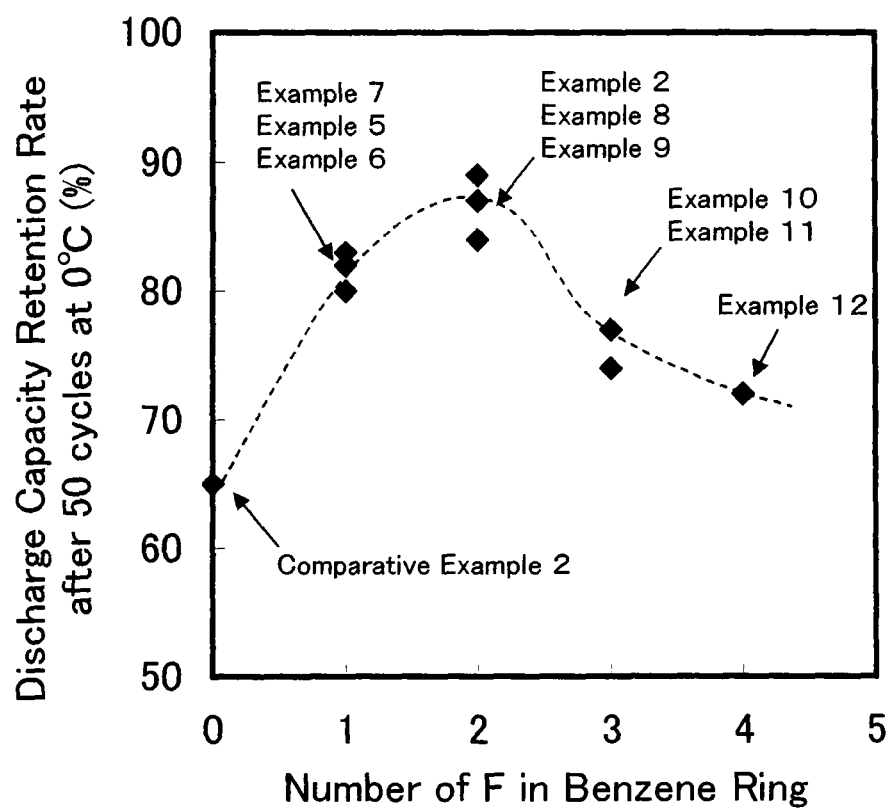

PHENYL SULFONATE COMPOUND, NONAQUEOUS ELECTROLYTE SOLUTION USING THE SAME, AND LITHIUM BATTERY

TECHNICAL FIELD

The present invention relates to a phenyl sulfonate compound useful as intermediate materials for medicines, agricultural chemicals, electronic materials, polymer materials and the like, or as battery materials, as well as to a nonaqueous electrolytic solution and a lithium battery which is excellent in low-temperature cycle property.

BACKGROUND ART

In recent years, lithium secondary batteries have been widely used as power supplies for electronic devices such as mobile telephones, notebook-size personal computers and the like, and also as power supplies for electric vehicles and for electric power storage, etc. These electronic devices and vehicles may be used in a broad temperature range, for example, at midsummer high temperatures or at frigid low temperatures, and are therefore required to have an improved cycle property in a broad temperature range.

A lithium secondary battery is mainly constituted of a positive electrode and a negative electrode containing a material capable of absorbing and releasing lithium, and a nonaqueous electrolytic solution containing a lithium salt and a nonaqueous solvent. As the nonaqueous solvent, used are carbonates such as ethylene carbonate (EC), propylene carbonate (PC), etc.

As the negative electrode, known are metal lithium, and metal compounds and carbon materials capable of absorbing and releasing lithium. In particular, lithium secondary batteries using a carbon material capable of absorbing and releasing lithium such as coke, artificial graphite, natural graphite or the like have been widely put into practical use.

It is known that, in the lithium secondary battery using a highly-crystalline carbon material such as artificial graphite, natural graphite or the like as the negative electrode material, the decomposed product or gas generated through reductive decomposition of the solvent in the nonaqueous electrolytic solution on the surface of the negative electrode during charging detracts from the electrochemical reaction favorable for the battery, therefore worsening the cycle property of the battery. Deposition of the decomposed product of the nonaqueous solvent interferes with smooth absorption and release of lithium by the negative electrode, and therefore, in particular, the cycle property at low temperatures may be thereby often worsened.

In addition, it is known that a lithium secondary battery using a lithium metal or its alloy, or a metal elemental substance such as tin, silicon or the like or its metal oxide as the negative electrode material may have a high initial battery capacity but its battery performance such as battery capacity and cycle property greatly worsens, since the micronized powdering of the material is promoted during cycles thereby bringing about accelerated reductive decomposition of the nonaqueous solvent, as compared with the negative electrode of a carbon material. In addition, the micronized powdering of the negative electrode material and the deposition of the decomposed product of the nonaqueous solvent may interfere with smooth absorption and release of lithium by the negative electrode, and therefore, in particular, the cycle property at low temperatures may be thereby often worsened.

On the other hand, it is known that, in a lithium secondary battery using, for example, $LiCoO_2$, $LiMn_2O_4$, $LiNiO_2$, $LiFePO_4$ or the like as the positive electrode, when the nonaqueous solvent in the nonaqueous electrolytic solution is heated at a high temperature in the charged state, the decomposed product or gas thereby locally generated through partial oxidative decomposition in the interface between the positive electrode material and the nonaqueous electrolytic solution interferes with the electrochemical reaction favorable for the battery, and therefore the battery performance such as cycle property is thereby also worsened.

As in the above, the decomposed product or gas generated through decomposition of the nonaqueous electrolytic solution on the negative electrode or the positive electrode interferes with the movement of lithium ions or swells the battery, and the battery performance is thereby worsened. Despite the situation, electronic appliances equipped with lithium secondary batteries therein are offering more and more an increasing range of functions and are being in a stream of further increase in the power consumption. With that, the capacity of lithium secondary batteries is being much increased, and the space volume for the nonaqueous electrolytic solution in the battery is decreased by increasing the density of the electrode and by reducing the useless space volume in the battery. Accordingly, the situation is that even decomposition of only a small amount of the nonaqueous electrolytic solution may worsen the battery performance at low temperatures.

JP-A 11-162511 discloses a lithium secondary battery with a nonaqueous electrolytic solution, which contains a compound having an S—O bond as the organic solvent therein and in which the material of the collector for the positive electrode and the material of the part of the outer casing that is in contact with the electrolytic solution on the positive electrode side is a valve metal or its alloy. In the paragraph [0018] of the patent publication, a phenyl methanesulfonate compound as an example of the compound having an S—O bond is disclosed, and the battery capacity in the initial stage at 25° C. and the cycle property are shown; however, the cycle property is not sufficiently satisfactory.

As a lithium primary battery, for example, there is known a lithium primary battery comprising manganese dioxide or graphite fluoride as the positive electrode and a lithium metal as the negative electrode, and this is widely used as having a high energy density. It is desired to inhibit the increase in the internal resistance of the battery during long-term storage and to improve the discharge load characteristic thereof at room temperature or low temperatures.

Recently, further, as a novel power source for electric vehicles or hybrid electric vehicles, electric storage devices have been developed, for example, an electric double layer capacitor using activated carbon or the like as the electrode from the viewpoint of the output power density thereof, and a so-called hybrid capacitor comprising a combination of the electric storage principle of a lithium ion secondary battery and that of an electric double layer capacitor (both the capacity by lithium absorption and release and the electric double layer capacity are utilized) from the viewpoint of both the energy density and the output power density thereof; and it is desired to improve the characteristics, especially the low-temperature cycle property of these capacitors.

DISCLOSURE OF THE INVENTION

An object of the present invention is to provide a specific phenyl sulfonate compound useful as intermediate materials for medicines, agricultural chemicals, electronic materials, polymer materials and the like, or as battery materials, and to provide a nonaqueous electrolytic solution capable of improving the low-temperature cycle property, and a lithium battery using it.

The present inventors have assiduously studied for the purpose of solving the above-mentioned problems and, as a result, have found that, in a nonaqueous electrolytic solution containing an electrolyte salt dissolved in a nonaqueous solvent, when a phenyl sulfonate compound in which the benzene ring has from 1 to 4 fluorine atoms and the oxygen atom of the sulfonate group directly bonds to the benzene ring is added to the nonaqueous electrolytic solution, then the low-temperature cycle property can be improved, and have completed the present invention.

Specifically, the present invention provides the following (1) to (3):

(1) A phenyl sulfonate compound represented by the following general formula (I):

[Formula 1]

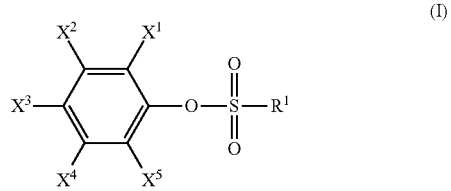

(wherein $X^1$ to $X^5$ each independently represents a fluorine atom or a hydrogen atom, and from two to four of these are fluorine atoms; $R^1$ represents a linear or branched alkyl group having from 1 to 6 carbon atoms, a linear or branched alkyl group having from 1 to 6 carbon atoms in which at least one hydrogen atom is substituted with a halogen atom, or an aryl group having from 6 to 9 carbon atoms).

(2) A nonaqueous electrolytic solution comprising an electrolyte salt dissolved in a nonaqueous solvent and containing a phenyl sulfonate compound represented by the following general formula (II) in an amount of from 0.01 to 10% by mass of the nonaqueous electrolytic solution:

[Formula 2]

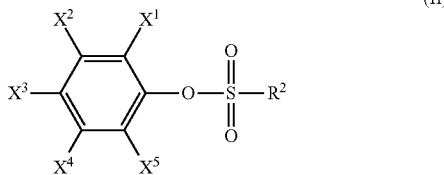

(wherein $X^1$ to $X^5$ each independently represents a fluorine atom or a hydrogen atom, and from one to four of these are fluorine atoms; $R^2$ represents a linear or branched alkyl group having from 1 to 6 carbon atoms, a linear or branched alkyl group having from 1 to 6 carbon atoms in which at least one hydrogen atom is substituted with a halogen atom, or an aryl group having from 6 to 9 carbon atoms).

(3) A lithium battery comprising a positive electrode, a negative electrode and a nonaqueous electrolytic solution of an electrolyte salt dissolved in a nonaqueous solvent, wherein the nonaqueous electrolytic solution contains a phenyl sulfonate compound of the above-mentioned general formula (II) in an amount of from 0.01 to 10% by mass of the nonaqueous electrolytic solution.

According to the present invention, there are provided a novel phenyl sulfonate compound useful as intermediate materials for medicines, agricultural chemicals, electronic materials, polymer materials and the like, or as battery materials, a nonaqueous electrolytic solution capable of improving the low-temperature cycle property, and a lithium battery using it.

BRIEF DESCRIPTION OF THE DRAWING

FIG. 1 This is a graph showing the relationship between the number of fluorine atoms on the benzene ring and the low-temperature cycle property.

BEST MODE FOR CARRYING OUT THE INVENTION

[Phenyl Sulfonate Compound]
The phenyl sulfonate compound of the present invention is a novel compound represented by the following general formula (I):

[Formula 3]

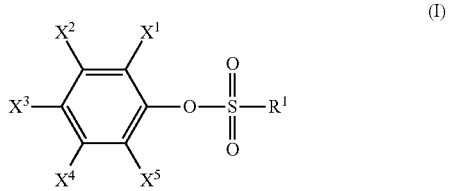

In the general formula (I), $X^1$ to $X^5$ each independently represents a fluorine atom or a hydrogen atom, and from two to four of these are fluorine atoms; $R^1$ represents a linear or branched alkyl group having from 1 to 6 carbon atoms, a linear or branched alkyl group having from 1 to 6 carbon atoms in which at least one hydrogen atom is substituted with a halogen atom, or an aryl group having from 6 to 9 carbon atoms.

The linear or branched alkyl group having from 1 to 6 carbon atoms for $R^1$ in the general formula (I) includes a methyl group, an ethyl group, an n-propyl group, an isopropyl group, an n-butyl group, an isobutyl group, a sec-butyl group, a tert-butyl group, an n-pentyl group, a neopentyl group, a sec-pentyl group, a tert-pentyl group, an n-hexyl group, a 2-hexyl group, etc. The linear or branched alkyl group having from 1 to 6 carbon atoms in which at least one hydrogen atom is substituted with a halogen atom may be a substituent of the above-mentioned alkyl group in which at least one hydrogen atom is substituted with a halogen atom, and its concrete examples include a trifluoromethyl group, and a 2,2,2-trifluoroethyl group.

The aryl group having from 6 to 9 carbon atoms for $R^1$ in the general formula (I) includes a phenyl group, a tosyl group, a mesityl group, etc.

$R^1$ in the general formula (I) is preferably a methyl group, an ethyl group, a trifluoromethyl group or a phenyl group from the viewpoint of the effect of the compound for improving the low-temperature cycle property in using it in a nonaqueous electrolytic solution, more preferably a methyl group.

Preferred examples of the phenyl sulfonate compound of the general formula (I) in which $R^1$ is a methyl group include 2,3-difluorophenyl methanesulfonate, 2,4-difluorophenyl methanesulfonate, 2,5-difluorophenyl methanesulfonate, 2,6-difluorophenyl methanesulfonate, 3,4-difluorophenyl methanesulfonate, 3,5-difluorophenyl methanesulfonate, 2,3,4-trifluorophenyl methanesulfonate, 2,3,5-trifluorophenyl methanesulfonate, 2,3,6-trifluorophenyl methanesulfonate, 2,4,5-trifluorophenyl methanesulfonate, 2,4,6-trifluorophenyl methanesulfonate, 3,4,5-trifluorophenyl methanesulfonate, 2,3,5,6-tetrafluorophenyl methanesulfonate, etc.

Also preferred are phenyl sulfonate compounds corresponding to the above in which $R^1$ is an ethyl group, an n-propyl group, an isopropyl group, an n-butyl group, an isobutyl group, a sec-butyl group, a tert-butyl group, an n-pentyl group, a neopentyl group, a sec-pentyl group, a tert-pentyl group, an n-hexyl group, a 2-hexyl group, etc.

[Production of Phenyl Sulfonate Compound of General Formula (I)]

The phenyl sulfonate compound, especially a fluorophenyl alkanesulfonate compound represented by the general formula (I) may be produced by reacting a fluorophenol compound with an alkanesulfonyl halide or an alkanesulfonic acid anhydride for esterification in the presence of a base in a solvent or in the absence of a solvent; however, the production is not limited to the method.

The fluorophenol compound includes 2,3-difluorophenol, 2,4-difluorophenol, 2,5-difluorophenol, 2,6-difluorophenol, 3,4-difluorophenol, 3,5-difluorophenol, 2,3,4-trifluorophenol, 2,3,5-trifluorophenol, 2,3,6-trifluorophenol, 2,4,5-trifluorophenol, 2,4,6-trifluorophenol, 3,4,5-trifluorophenol, 2,3,5,6-tetrafluorophenol, etc.

The alkanesulfonyl halide includes methanesulfonyl chloride, ethanesulfonyl chloride, trifluoromethanesulfonyl chloride, methanesulfonyl bromide, ethanesulfonyl bromide, trifluoromethanesulfonyl bromide, etc.

The alkanesulfonic acid anhydride includes methanesulfonic acid anhydride, ethanesulfonic acid anhydride, trifluoromethanesulfonic acid anhydride, etc.

The amount of the alkanesulfonyl halide or the alkanesulfonic acid anhydride to be used is preferably from 0.9 to 10 mols, more preferably from 1 to 3 mols, most preferably from 1 to 1.5 mols relative to 1 mol of the fluorophenol compound.

The solvent to be used may be any one inert to the reaction, and is not specifically defined. For example, it includes aliphatic hydrocarbons such as hexane, heptane, etc.; halogenohydrocarbons such as dichloroethane, dichloropropane, etc.; aromatic hydrocarbons such as toluene, xylene, etc.; halogenoaromatic hydrocarbons such as chlorobenzene, fluorobenzene, etc.; ethers such as diethyl ether, etc.; nitriles such as acetonitrile, propionitrile, etc.; amides such as N,N-dimethylformamide, etc.; sulfoxides such as dimethyl sulfoxide, etc.; nitro compounds such as nitromethane, nitroethane, etc.; ketones such as acetone, methyl ethyl ketone, methyl isobutyl ketone, cyclohexanone, etc.; esters such as ethyl acetate, dimethyl carbonate, etc.; water, and their mixtures. Especially preferred are toluene, and xylene.

The amount of the solvent to be used is preferably from 0 to 30 parts by mass, more preferably from 1 to 15 parts by mass relative to 1 part by mass of the fluorophenol compound.

As the base, any of an inorganic base or an organic base may be used herein.

The inorganic base includes potassium hydroxide, potassium carbonate, potassium hydride, potassium metal, sodium hydroxide, sodium carbonate, sodium hydride, sodium metal, calcium hydroxide, calcium oxide, calcium hydride, lithium hydroxide, lithium carbonate, lithium hydride, lithium metal, etc.

The organic base includes linear or branched tertiary amines, mono- or poly-substituted pyrroles, pyrrolidones, imidazoles, imidazolidinones, pyridines, pyrimidines, quinolines, N,N-dialkylcarboxyamides; and especially preferred are trialkylamines such as trimethylamine, triethylamine, tripropylamine, tributylamine, ethyldiisopropylamine, etc., as well as pyridine, N-methylpyrrolidone, N,N-dimethylacetamide, N,N-dimethylaminopyridine, and 1,3-dimethylimidazolidinone.

One or more such bases may be used herein either singly or as combined.

The amount of the base to be used is preferably from 0.8 to 5 mols, more preferably from 1 to 3 mols, even more preferably from 1 to 1.5 mols relative to 1 mol of the fluorophenol compound as the production of side products can be prevented.

In the reaction of the fluorophenol compound and the alkanesulfonyl halide or alkanesulfonic acid anhydride, the lowermost limit of the reaction temperature is preferably −70° C. or higher, more preferably −20° C. or higher in order not to lower the reactivity. The uppermost limit of the reaction temperature is preferably 80° C. or lower, more preferably 60° C. or lower in order to prevent side reaction or prevent decomposition of the product.

The reaction time may depend on the reaction temperature and the reactions scale; however, when the reaction time is too short, unreacted substances may remain; but on the contrary, when the reaction time is too long, then the product may decompose or side reaction may occur. Therefore, the reaction time is preferably from 0.1 to 12 hours, more preferably from 0.2 to 6 hours. The reaction pressure may fall within a range of from 0.1 to 10 atm, preferably from 0.5 to 5 atm.

[Nonaqueous Electrolytic Solution]

The nonaqueous electrolytic solution of the present invention is a nonaqueous electrolytic solution of an electrolyte salt dissolved in a nonaqueous solvent, and is characterized by containing a phenylsulfonyl compound represented by the following general formula (II) in an amount of from 0.01 to 10% by mass of the nonaqueous electrolytic solution.

[Formula 4]

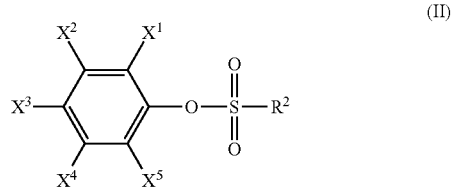

(II)

In the general formula (II), $X^1$ to $X^5$ each independently represents a fluorine atom or a hydrogen atom, and from one to four of these are fluorine atoms; $R^2$ represents a linear or branched alkyl group having from 1 to 6 carbon atoms, a linear or branched alkyl group having from 1 to 6 carbon atoms in which at least one hydrogen atom is substituted with a halogen atom, or an aryl group having from 6 to 9 carbon atoms.

The linear or branched alkyl group having from 1 to 6 carbon atoms for $R^2$ in the general formula (II) includes a methyl group, an ethyl group, an n-propyl group, an isopropyl group, an n-butyl group, an isobutyl group, a sec-butyl group, a tert-butyl group, an n-pentyl group, a neopentyl group, a sec-pentyl group, a tert-pentyl group, an n-hexyl group, a 2-hexyl group, etc. The linear or branched alkyl group having from 1 to 6 carbon atoms in which at least one hydrogen atom is substituted with a halogen atom may be a substituent of the above-mentioned alkyl group in which at least one hydrogen atom is substituted with a halogen atom, and its concrete examples include a trifluoromethyl group, and a 2,2,2-trifluoroethyl group.

The aryl group having from 6 to 9 carbon atoms for $R^2$ in the general formula (II) includes a phenyl group, a tosyl group, a mesityl group, etc.

$R^2$ in the general formula (II) is preferably a methyl group, an ethyl group, a trifluoromethyl group or a phenyl group from the viewpoint of the effect of the compound for improving the low-temperature cycle property, more preferably a methyl group.

Preferred examples of the phenyl sulfonate compound of the general formula (II) in which $R^2$ is a methyl group include 2-fluorophenyl methanesulfonate, 3-fluorophenyl methanesulfonate, 4-fluorophenyl methanesulfonate, 2,3-difluorophenyl methanesulfonate, 2,4-difluorophenyl methanesulfonate, 2,5-difluorophenyl methanesulfonate, 2,6-difluorophenyl methanesulfonate, 3,4-difluorophenyl methanesulfonate, 3,5-difluorophenyl methanesulfonate, 2,3,4-trifluorophenyl methanesulfonate, 2,3,5-trifluorophenyl methanesulfonate, 2,3,6-trifluorophenyl methanesulfonate, 2,4,5-trifluorophenyl methanesulfonate, 2,4,6-trifluorophenyl methanesulfonate, 3,4,5-trifluorophenyl methanesulfonate, 2,3,5,6-tetrafluorophenyl methanesulfonate, etc.

Also preferred are phenyl sulfonate compounds corresponding to the above in which $R^2$ is an ethyl group, an n-propyl group, an isopropyl group, an n-butyl group, an isobutyl group, a sec-butyl group, a tert-butyl group, an n-pentyl group, a neopentyl group, a sec-pentyl group, a tert-pentyl group, an n-hexyl group, or a 2-hexyl group.

The phenyl sulfonate compound, especially a fluorophenyl alkanesulfonate compound represented by the general formula (II) may be produced by reacting a fluorophenol compound with an alkanesulfonyl halide or an alkanesulfonic acid anhydride for esterification in the presence of a base in a solvent or in the absence of a solvent, like in the production method for the phenyl sulfonate compound of the general formula (I). Its concrete example and preferred example are the same as above, and describing them herein is omitted. In this case, as the fluorophenol compound, also usable are 2-fluorophenol, 3-fluorophenol, 4-fluorophenol, etc., in addition to the above-exemplified ones.

The compound of the general formula (II) where from one to four of $X^1$ to $X^5$ are fluorine atoms can improve the low-temperature cycle property, and its reason may be considered as follows: Specifically, decomposition of the phenyl sulfonate compound of the present invention can induce a fluorine atom-containing, stable surface film on a negative electrode, and therefore the solvent in the nonaqueous electrolytic solution is prevented from being decomposed. At the same time, in particular, when the compound has one or two fluorine atoms, the polymerization of the benzene ring is not promoted too excessively even when the fluorine atoms are released through the decomposition of the phenyl sulfonate compound, and therefore, a flexible surface film can be formed on the negative electrode. Accordingly, absorption and release of lithium ions at low temperatures could be effected smoothly, and the low-temperature cycle property can be significantly improved.

When the compound has two fluorine atoms on the benzene ring, its effect of improving the low-temperature cycle property is the highest. With the increase in the number of the fluorine atoms on the benzene ring, the polymerization of the benzene ring is promoted more, and therefore, the surface film on the negative electrode may be rigid and the effect of the compound for improving the low-temperature cycle property may be lower. Accordingly, the number of the fluorine atoms is preferably at most 4. Specifically, the number of the fluorine atoms on the benzene ring in the general formula (II) is most preferably 2, but next to it, the benzene ring preferably has one fluorine, and further next to it, the benzene ring has three fluorine atoms.

The effect of the compound for improving the low-temperature cycle property may depend on the position of the fluorine atom therein. When the compound has a fluorine atom at the ortho-position and the para-position, then it is preferred as the compound well improves the low-temperature cycle property, and more preferably, the compound has a fluorine atom at the para-position.

In the nonaqueous electrolytic solution of the present invention, the effect for improving the low-temperature cycle property by the phenyl sulfonate compound of the general formula (II) is an effect peculiar to the compound having a sulfone group with an oxygen atom directly bonding to the benzene ring, or that is having a sulfonyloxy group directly bonding thereto.

For example, a benzenesulfonate in which the sulfur atom directly bonds to the benzene ring, or a benzenesulfonate with a carbon atom directly bonding to the benzene ring has no effect for improving the low-temperature cycle property. Though not always clear, the reason may be considered as follows: The phenyl sulfonate compound with an oxygen atom directly bonding to the benzene ring may form a surface film having an oxygen atom bonding to the benzene ring on the electrode, therefore expressing the effect of smoothly moving lithium ions.

Regarding the amount of the compound of the general formula (II) in the nonaqueous electrolytic solution of the present invention, when the amount is more than 10% by mass, then the surface film may be formed too excessively on the electrode and therefore, the low-temperature cycle property may be rather worsened; but when the amount is less than 0.01% by mass, the surface film could not be formed sufficiently, and therefore the compound would be ineffective for improving the low-temperature cycle property. Accordingly, the content of the compound is at least 0.01% by mass of the nonaqueous electrolytic solution (that is, the content of the compound is at least 0.01% by mass relative to the mass of the nonaqueous electrolytic solution), preferably at least 0.1% by mass, more preferably at least 0.2% by mass, even more preferably at least 0.3% by mass. Its uppermost limit is at most 10% by mass, preferably at most 7% by mass, more preferably at most 5% by mass, even more preferably at most 3% by mass.

In the nonaqueous electrolytic solution of the present invention, the compound of the general formula (II) can exhibit its effect of improving the low-temperature cycle property even when used alone in the solution, but when combined with any of a nonaqueous solvent, an electrolyte salt and further other additives to be mentioned below, the compound exhibits a specific effect of synergistically improving the low-temperature cycle property. Though not always clear, the reason may be considered because a mixed surface film having a high ionic conductivity, which contains the fluorine of the compound of the general formula (II) and contains an element different from fluorine, is formed whereby the solvent in the nonaqueous electrolytic solution can be more effectively prevented from being decomposed on the electrode surface of the positive and negative electrodes.

[Nonaqueous Solvent]

The nonaqueous solvent for use in the nonaqueous electrolytic solution of the present invention includes cyclic carbonates, linear carbonates, linear esters, ethers, amides, phosphates, sulfones, lactones, nitriles, S=O bond-containing compounds except the phenyl sulfonate compound of the present invention, etc.

The cyclic carbonates include ethylene carbonate (EC), propylene carbonate (PC), butylene carbonate (BC), 4-fluoro-1,3-dioxolan-2-one (FEC), trans or cis-4,5-difluoro-1,3-dioxolan-2-one (hereinafter the two are collectively referred to as "DFEC"), vinylene carbonate (VC), vinylethylene carbonate (VEC), etc. Of those cyclic carbonates, FEC, VC and VEC are preferred as the cycle property can be improved; and PC is preferred as the low-temperature cycle property can be improved. In general, FEC, DFEC, VC and VEC may worsen the low-temperature cycle property, but the nonaqueous electrolytic solution containing any of these along with the sulfone compound of the present invention may have improved low-temperature cycle property.

One type of those solvents may be used, but using two or more different types as combined is preferred as further improving the low-temperature cycle property. Preferred combinations of the cyclic carbonates include EC and PC; EC and VC; PC and VC; FEC and VC; FEC and EC; FEC and PC; DFEC and EC; DFEC and PC; DFEC and VC; DFEC and VEC; etc. Of these combinations, more preferred are EC and VC; FEC and PC; and DFEC and PC.

Not specifically defined, the content of the cyclic carbonate is preferably from 10 to 40% by volume relative to the total volume of the nonaqueous solvent. When the content is less than 10% by volume, then the conductivity of the nonaqueous electrolytic solution may lower; but when more than 40% by volume, then the viscosity of the nonaqueous electrolytic solution may increase and the low-temperature cycle property may worsen. Accordingly, the above range is preferred.

The linear carbonates include asymmetric linear carbonates such as methyl ethyl carbonate (MEC), methyl propyl carbonate, methyl isopropyl carbonate, methyl butyl carbonate, ethyl propyl carbonate, etc.; symmetric linear carbonates such as dimethyl carbonate (DMC), diethyl carbonate (DEC), dipropyl carbonate, dibutyl carbonate, etc. In particular, the asymmetric carbonates are preferred, as effectively improving the low-temperature cycle property. One type of those solvents may be used, but using two or more different types as combined is preferred as further improving the low-temperature cycle property.

Not specifically defined, the content of the linear carbonate is preferably from 60 to 90% by volume relative to the total volume of the nonaqueous solvent. When the content is less than 60% by volume, then the viscosity of the nonaqueous electrolytic solution may increase; but when more than 90% by volume, then the electric conductivity of the nonaqueous electrolytic solution may lower and the low-temperature cycle property may worsen. Accordingly, the above range is preferred.

The linear esters include methyl propionate, methyl pivalate, butyl pivalate, hexyl pivalate, octyl pivalate, dimethyl oxalate, ethyl methyl oxalate, diethyl oxalate, etc. The ethers include tetrahydrofuran, 2-methyltetrahydrofuran, 1,3-dioxane, 1,4-dioxane, 1,2-dimethoxyethane, 1,2-diethoxyethane, 1,2-dibutoxyethane, etc.

The amides include dimethylformamide, etc.; the phosphates include trimethyl phosphate, tributyl phosphate, trioctyl phosphate, etc.; the sulfones include sulfolane, etc.; the lactones include γ-butyrolactone, γ-valerolactone, α-angelicalactone, etc.; the nitriles include acetonitrile, propionitrile, succinonitrile, adiponitrile, etc.

The S=O bond-containing compounds except the phenyl sulfonate compound of the present invention include 1,3-propanesultone (PS), ethylene sulfite, 1,2-cyclohexanediol cyclic sulfite, 5-vinyl-hexahydro-1,3,2-benzodioxathiol-2-oxide, 1,4-butanediol dimethanesulfonate, 1,3-butanediol dimethanesulfonate, divinyl sulfone, 1,2-bis(vinylsulfonyl) ethane, bis(2-vinylsulfonylethyl) ether, etc.

In general, the S=O bond-containing compounds may worsen the low-temperature cycle property; however, when using them as combined with the phenyl sulfonate compound of the present invention is favorable as improving the low-temperature cycle property. Regarding the content of the S=O bond-containing compound except the phenyl sulfonate compound of the present invention, when the content thereof is more than 10% by mass of the nonaqueous electrolytic solution, then the low-temperature cycle property may worsen; but when less than 0.01% by mass, the effect of improving the low-temperature cycle property could not be sufficiently attained. Accordingly, the content of the S=O bond-containing compound is preferably at least 0.01% by mass of the nonaqueous electrolytic solution, more preferably at least 0.1% by mass, even more preferably at least 0.5% by mass. The uppermost limit of the content is preferably at most 10% by mass, more preferably at most 5% by mass, even more preferably at most 3% by mass.

In general, the nonaqueous solvents are used as a mixture thereof for attaining the suitable physical properties. Regarding their combinations, for example, there are mentioned a combination of a cyclic carbonate and a linear carbonate, a combination of a cyclic carbonate, a linear carbonate and a lactone, a combination of a cyclic carbonate, a linear carbonate and an ether, a combination of a cyclic carbonate, a linear carbonate and a linear ester, a combination of a cyclic carbonate, a linear carbonate and a nitrile, a combination of a cyclic carbonate, a linear carbonate and the above-mentioned S=O bond-containing compound, etc.

Of those, preferred is using a nonaqueous solvent of a combination of at least a cyclic carbonate and a linear carbonate, as effectively improving the low-temperature cycle property. The ratio of the cyclic carbonate to the linear carbonate is not specifically defined. Preferably, the ratio (by volume) of cyclic carbonate/linear carbonate is from 10/90 to 40/60, more preferably from 15/85 to 35/65, even more preferably from 20/80 to 30/70.

[Electrolyte Salt]

The electrolyte salt for use in the nonaqueous electrolytic solution of the present invention includes Li salts such as $LiPF_6$, $LiBF_4$, $LiClO_4$, etc.; linear alkyl group-having lithium salts such as $LiN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$, $LiPF_5(iso-C_3F_7)$, etc.; cyclic alkylene chain-having lithium salts such as $(CF_2)_2(SO_2)_2NLi$, $(CF_2)_3(SO_2)_2NLi$, etc.; and lithium salts with an anion of an oxalate complex such as lithium bis[oxalate-O,O']borate, lithium difluoro[oxalate-O,O']borate, etc. Of those, especially preferred electrolyte salts are $LiPF_6$, $LiBF_4$, $LiN(SO_2CF_3)_2$, $LiN(SO_2C_2F_5)_2$; and most preferred electrolyte salts are $LiPF_6$, $LiBF_4$ and $LiN(SO_2CF_3)_2$. One or more of these electrolyte salts may be used herein either singly or as combined.

A preferred combination of these electrolyte salts is a combination containing $LiPF_6$ as combined with at least one selected from $LiBF_4$, $LiN(SO_2CF_3)_2$ and $LiN(SO_2C_2F_5)_2$. Preferred are a combination of $LiPF_6$ and $LiBF_4$; a combination of $LiPF_6$ and $LiN(SO_2CF_3)_2$; a combination of $LiPF_6$ and $LiN(SO_2C_2F_5)_2$, etc.

When the ratio (by mol) of $LiPF_6/[LiBF_4$ or $LiN(SO_2CF_3)_2$ or $LiN(SO_2C_2F_5)_2]$ is smaller than 70/30 in point of the proportion of $LiPF_6$, or when the ratio is larger than 99/1 in point of the proportion of $LiPF_6$, then the low-temperature cycle property may worsen. Accordingly, the ratio (by mol) of LiPF$_6$/[LiBF$_4$ or LiN(SO$_2$CF$_3$)$_2$ or LiN(SO$_2$C$_2$F$_5$)$_2$] is preferably within a range of from 70/30 to 99/1, more preferably from 80/20 to 98/2. The combination falling within the above range is more effective for bettering the low-temperature cycle property.

The electrolyte salts may be combined in any desired ratio. In the combination of LiPF$_6$ with any of LiBF$_4$, LiN(SO$_2$CF$_3$)$_2$ and LiN(SO$_2$C$_2$F$_5$)$_2$, when the proportion (as molar fraction) of the other electrolyte salt than those ingredients to the total electrolyte salts is less than 0.01%, then the effect of improving the low-temperature cycle property may be poor; but when it is more than 45%, then the low-temperature cycle property may worsen. Accordingly, the proportion (as molar fraction) is preferably from 0.01 to 45%, more preferably from 0.03 to 20%, even more preferably from 0.05 to 10%, most preferably from 0.05 to 5%.

The concentration of all these electrolyte salts as dissolved in the solution is generally preferably at least 0.3 M relative to the above-mentioned nonaqueous solvent, more preferably at least 0.5 M, most preferably at least 0.7 M. The uppermost limit of the concentration is preferably at most 2.5 M, more preferably at most 2.0 M, even more preferably at most 1.5 M.

As the electrolyte for electric double layer capacitors, usable are known quaternary ammonium salts such as tetraethylammonium tetrafluoroborate, triethylmethyl ammonium tetrafluoroborate, tetraethylammonium hexafluorophosphate, etc.

[Other Additives]

An aromatic compound may be added to the nonaqueous electrolytic solution of the present invention, thereby securing the safety of the battery in overcharging. Preferred examples of the aromatic compound include cyclohexylbenzene, fluorocyclohexylbenzene compound (1-fluoro-2-cyclohexylbenzene, 1-fluoro-3-cyclohexylbenzene, 1-fluoro-4-cyclohexylbenzene), tert-butylbenzene, tert-amylbenzene, 1-fluoro-4-tert-butylbenzene, 1,3-di-tert-butylbenzene, biphenyl, terphenyl (o-, m-, p-form), diphenyl ether, fluorobenzene, difluorobenzene (o-, m-, p-form), 2,4-difluoroanisole, partially hydrogenated (1,2-dicyclohexylbenzene, 2-phenylbicyclohexyl, 1,2-diphenylcyclohexane, o-cyclohexylbiphenyl), etc. One or more of these compounds may be used herein either singly or as combined.

[Production of Nonaqueous Electrolytic Solution]

The nonaqueous electrolytic solution of the present invention can be produced, for example, by mixing the above-mentioned nonaqueous solvents followed by dissolving therein the above-mentioned electrolyte salt and the compound of the general formula (II) in an amount of from 0.01 to 10% by mass of the resulting nonaqueous electrolytic solution.

In this case, the compounds to be added to the nonaqueous solvent and the electrolytic solution are preferably previously purified within a range not significantly detracting from the producibility, in which, therefore, the impurity content is preferably as low as possible.

For example, air or carbon dioxide may be incorporated into the nonaqueous electrolytic solution of the present invention to thereby prevent gas generation resulting from decomposition of the electrolytic solution and to enhance the battery characteristics such as the long-term cycle property and the charge storage property in the charged state.

In the present invention, from the viewpoint of improving the charging and discharging characteristics at high temperatures, the nonaqueous electrolytic solution preferably contains carbon dioxide as dissolved therein. The amount of carbon dioxide to be dissolved in the nonaqueous electrolytic solution is preferably at least 0.001 by mass of the solution, more preferably at least 0.05% by mass, even more preferably at least 0.2% by mass; and most preferably, carbon dioxide is dissolved in the nonaqueous electrolytic solution until its saturation therein.

The nonaqueous electrolytic solution of the present invention is favorably used for the electrolytic solution for lithium primary batteries and lithium secondary batteries. Further, the nonaqueous electrolytic solution of the present invention is also usable as an electrolytic solution for electric double layer capacitors or as an electrolytic solution for hybrid capacitors. Of those, the nonaqueous electrolytic solution of the present invention is most favorable for lithium secondary batteries.

[Lithium Battery]

The lithium battery of the present invention collectively includes a lithium primary battery and a lithium secondary battery, comprising a positive electrode, a negative electrode and the above-mentioned nonaqueous electrolytic solution of an electrolyte salt dissolved in a nonaqueous solvent, and is characterized in that a phenyl sulfonate compound of the above-mentioned general formula (II) is in the nonaqueous electrolytic solution in an amount of from 0.01 to 10% by mass of the nonaqueous electrolytic solution.

In the lithium battery of the present invention, the other constitutive components such as a positive electrode and a negative electrode except for the nonaqueous electrolytic solution can be used with no limitation.

For example, as the positive electrode active material for lithium secondary battery, usable are complex metal oxides of lithium containing any of cobalt, manganese or nickel. One or more such positive electrode active materials may be used either singly or as combined.

The complex metal oxides include, for example, LiCoO$_2$, LiMn$_2$O$_4$, LiNiO$_2$, LiCO$_{1-x}$Ni$_x$O$_2$ (0.01<x<1), LiCO$_{1/3}$Ni$_{1/3}$Mn$_{1/3}$O$_2$, LiNi$_{1/2}$Mn$_{3/2}$O$_4$, LiCp$_{0.98}$Mg$_{0.02}$O$_2$, etc. Combinations of LiCoO$_2$ and LiMn$_2$O$_4$; LiCoO$_2$ and LiNiO$_2$; LiMn$_2$O$_4$ and LiNiO$_2$ are acceptable herein.

For enhancing the safety in overcharging or enhancing the cycle property, the lithium complex oxide may be partly substituted with any other element for enabling the use of the battery at a charging potential of 4.3 V or more. For example, a part of cobalt, manganese and nickel may be substituted with at least one element of Sn, Mg, Fe, Ti, Al, Zr, Cr, V, Ga, Zn, Cu, Bi, Mo, La, etc.; or O may be partly substituted with S or F; or the oxide may be coated with a compound containing such other element.

Of those, preferred are lithium complex metal oxides such as LiCoO$_2$, LiMn$_2$O$_4$ and LiNiO$_2$, with which the positive electrode charging potential in a full-charging state may be 4.3 V or more, based on Li. More preferred are lithium complex oxides usable at 4.4 V or more, such as LiCO$_{1-x}$M$_x$O$_2$ (where M is at least one element of Sn, Mg, Fe, Ti, Al, Zr, Cr, V, Ga, Zn and Cu; 0.001≦x≦0.05), LiCO$_{1/3}$Ni$_{1/3}$Mn$_{1/3}$O$_2$, and LiNi$_{1/2}$Mn$_{3/2}$O$_4$.

Further, lithium-containing olivine-type phosphates are also usable as the positive electrode active material. Their concrete examples include LiFePO$_4$, LiCoPO$_4$, LiNiPO$_4$, LiMnPO$_4$, etc.

The lithium-containing olivine-type phosphates may be partly substituted with any other element. For example, a part of iron, cobalt, nickel and manganese therein may be substituted with at least one element selected from Co, Mn, Ni, Mg, Al, B, Ti, V, Nb, Cu, Zn, Mo, Ca, Sr, W and Zr; or the phosphates may be coated with a compound containing any of these other elements or with a carbon material. Of those, preferred are LiFePO$_4$ and LiMnPO$_4$.

The lithium-containing olivine-type phosphate may be combined with, for example, the above-mentioned positive electrode active material.

For the positive electrode for lithium primary battery, there are mentioned oxides or chalcogen compounds of one or more metal elements such as CuO, $Cu_2O$, $Ag_2O$, $Ag_2CrO_4$, $CuS$, $CuSO_4$, $TiO_2$, $TiS_2$, $SiO_2$, SnO, $V_2O_5$, $V_6O_{12}$, $VO_x$, $Nb_2O_5$, $Bi_2O_3$, $Bi_2Pb_2O_5$, $Sb_2O_3$, $CrO_3$, $Cr_2O_3$, $MoO_3$, $WO_3$, $SeO_2$, $MnO_2$, $Mn_2O_3$, $Fe_2O_3$, FeO, $Fe_3O_4$, $Ni_2O_3$, NiO, $CoO_3$, CoO, etc.; sulfur compounds such as $SO_2$, $SOCl_2$, etc.; carbon fluorides (fluorographite) represented by a general formula $(CF_x)_n$, etc. Above all, preferred are $MnO_2$, $V_2O_5$, fluorographite, etc.

Not specifically defined, the electroconductive agent of the positive electrode may be any electron-transmitting material not undergoing chemical change. For example, it includes graphites such as natural graphite (flaky graphite, etc.), artificial graphite, etc.; carbon blacks such as acetylene black, Ketjen black, channel black, furnace black, lamp black, thermal black, etc. Graphites and carbon blacks may be combined suitably. The amount of the electroconductive agent to be added to the positive electrode mixture is preferably from 1 to 10% by mass, more preferably from 2 to 5% by mass.

The positive electrode may be formed by mixing the above-mentioned positive electrode active material with an electroconductive agent such as acetylene black, carbon black or the like, and with a binder such as polytetrafluoroethylene (PTFE), polyvinylidene fluoride (PVDF), styrene/butadiene copolymer (SBR), acrylonitrile/butadiene copolymer (NBR), carboxymethyl cellulose (CMC), ethylene/propylene/diene terpolymer or the like, then adding thereto a high-boiling-point solvent such as 1-methyl-2-pyrrolidone or the like, and kneading them to give a positive electrode mixture, thereafter applying the positive electrode mixture onto an aluminium foil or a stainless lath plate or the like serving as a collector, and drying and shaping it under pressure, and then heat-treating it in vacuum at a temperature of from 50° C. to 250° C. or so for about 2 hours.

The density of the part except the collector of the positive electrode may be generally at least 1.5 $g/cm^3$, and for further increasing the capacity of the battery, the density is preferably at least 2 $g/cm^3$, more preferably at least 3 $g/cm^3$, even more preferably at least 3.6 $g/cm^3$.

As the negative electrode active material for lithium secondary battery, usable are one or more of lithium metal, lithium alloys, carbon materials [graphites such as artificial graphite, natural graphite, etc.;] and metal compounds capable of absorbing and releasing lithium, either singly or as combined.

Of those, preferred are high-crystalline carbon materials such as artificial graphite, natural graphite or the like of which the ability of absorbing and releasing lithium ions is good. More preferred is a carbon material having a graphite-type crystal structure where the lattice (002) spacing ($d_{002}$) is at most 0.340 nm (nanometers), especially from 0.335 to 0.337 nm. More preferably, the high-crystalline carbon material is coated with a low-crystalline carbon material, as capable of improving the low-temperature cycle property. When such a high-crystalline carbon material is used, then it may react with a nonaqueous electrolytic solution in charging thereby worsening the low-temperature cycle property; however, in the lithium secondary battery of the present invention, the reaction with the nonaqueous electrolytic solution can be retarded.

The metal compound capable of absorbing and releasing lithium, serving as a negative electrode active material, includes compounds containing at least one metal element of Si, Ge, Sn, Pb, P, Sb, Bi, Al, Ga, In, Ti, Mn, Fe, Co, Ni, Cu, Zn, Ag, Mg, Sr, Ba, etc. These metal compounds may have any morphology of simple substances, alloys, oxides, nitrides, sulfides, borides, alloys with lithium or the like; but preferred are any of simple substances, alloys, oxides and alloys with lithium, as capable of increasing the battery capacity. Above all, more preferred are those containing at least one element selected from Si, Ge and Sn, and even more preferred are those containing at least one element selected from Si and Sn, as capable of increasing the capacity of the battery.

The negative electrode may be formed, using the same electroconductive agent, binder and high-boiling point solvent as in the formation of the above-mentioned positive electrode. These are mixed and kneaded to give a negative electrode mixture, then the negative electrode mixture is applied onto a copper foil or the like serving as a collector, then dried and shaped under pressure, and thereafter heat-treated in vacuum at a temperature of from 50° C. to 250° C. or so for about 2 hours.

As the negative electrode active material for lithium primary battery, usable is a lithium metal or a lithium alloy.

In case where graphite is used as the negative electrode active material, the density of the part except the collector of the negative electrode may be generally at least 1.4 $g/cm^3$, and for further increasing the capacity of the battery, the density is preferably at least 1.6 $g/cm^3$, more preferably at least 1.7 $g/cm^3$.

As the separator for battery, usable is a single-layer or laminate porous film of polyolefin such as polypropylene, polyethylene or the like, as well as a woven fabric, a nonwoven fabric, etc.

The structure of the lithium secondary battery is not specifically defined. The battery may be a coin-shaped battery, a cylindrical battery, a square-shaped battery, or a laminate-type battery, each having a single layered or multi-layered separator.

The lithium secondary battery of the present invention exhibits excellent long-term cycle property even when the final charging voltage is 4.2 V or higher and particularly 4.3 V or higher. Furthermore, the cycle property is good even when the final charging voltage is 4.4 V. The final discharging voltage can be 2.5 V or more and further 2.8 V or more. Not specifically defined, the current value may be generally within a range of from 0.1 to 3 C. The lithium secondary battery of the present invention may be charged and discharged at −40° C. to 100° C. and preferably at 0° C. to 80° C.

In the present invention, as a countermeasure against the increase in the internal pressure of the lithium secondary battery, there may be employed a method of providing a safety valve in the battery cap or a method of forming a cutout in the battery component such as the battery can, the gasket or the like. In addition, as a safety countermeasure against overcharging, a current breaker capable of detecting the internal pressure of the battery to cut off the current may be provided in the battery cap.

EXAMPLES

Production Example for the phenyl sulfonate compound of the present invention, and Examples of an electrolytic solution using it are shown below; however, the present invention should not be restricted by these Examples.

Production Example 1

Production of 2,4-difluorophenyl methanesulfonate 10.00 g (0.077 mol) of 2,4-difluorophenol, 100 mL of toluene and 8.17 g (0.081 mol) of triethylamine were mixed at 25° C., and with controlling the temperature of the reaction liquid to be at 20° C. or lower in an ice bath, 9.24 g (0.081 mol) of methanesulfonyl chloride was dropwise added thereto, taking 15 minutes, and these were reacted with stirring at 25° C. for 1 hour. Water was added to the reaction liquid to separate the organic layer, and the organic layer was washed twice with saturated sodium bicarbonate water and once with water, then dried with anhydrous $MgSO_4$ and subjected to distillation under reduced pressure (98° C./3 Torr) to give 15.1 g of 2,4-difluorophenyl methanesulfonate (yield 94%).

The obtained 2,4-difluorophenyl methanesulfonate was analyzed for $^1$H-NMR, $^{13}$C-NMR (using JEOL's Model AL300) and mass spectrometry (using Hitachi's Model M80B) to confirm its structure. The results are shown below.

(1) $^1$H-NMR (300 MHz, $CDCl_3$): δ=7.4-7.3 (m, 1H), 7.1-6.9 (m, 2H), 3.22 (s, 3H)

(2) $^{13}$C-NMR (75 MHz, $CDCl_3$): δ=161.0 (dxd, $J_{C-F}$=10.6×250.4 Hz), 154.5 (dxd, $J_{C-F}$=12.5×253.5 Hz), 133.0 (dxd, $J_{C-F}$=4.4×12.5 Hz), 126.0 (d, $J_{C-F}$=9.34 Hz), 112.0 (dxd, $J_{C-F}$=3.7×23.7 Hz), 105.7 (dxd, $J_{C-F}$=21.8× 26.8 Hz), 38.1

(3) Mass Spectrometry: MS (EI) m/z (%)=208 (31) [M$^+$], 130 (100), 129 (94), 101 (82), 79 (16), 51 (10)

Examples 1 to 4

(1) Preparation of Nonaqueous Electrolytic Solution $LiPF_6$ to be 1 M was dissolved in a nonaqueous solvent of EC/MEC/DMC=30/35/35 (ratio by volume), and further 2,4-difluorophenyl methanesulfonate was added thereto to prepare a nonaqueous electrolytic solution, in an amount of 0.1% by mass of the resulting nonaqueous electrolytic solution (Example 1), 1% by mass (Example 2), 5% by mass (Example 3) and 10% by mass (Example 4).

[Production of Lithium Ion Secondary Battery]

93% by mass of $LiCO_{0.98}Mg_{0.02})_2$ (positive electrode active material) and 3% by mass of acetylene black (electroconductive agent) were mixed, and added to and mixed with a solution previously prepared by dissolving 4% by mass of polyvinylidene fluoride (binder) in 1-methyl-2-pyrrolidone, thereby preparing a positive electrode mixture paste. The positive electrode mixture paste was applied onto both surfaces of an aluminium foil (collector), dried, processed under pressure and cut into a predetermined size, thereby producing a long rectangular, positive electrode sheet. The density of a part of the positive electrode except the collector was 3.6 g/cm$^3$.

95% by mass of artificial graphite ($d_{002}$=0.335 nm, negative electrode active material) coated with low-crystalline carbon was added to and mixed with a solution previously prepared by dissolving 5% by mass of polyvinylidene fluoride (binder) in 1-methyl-2-pyrrolidone, thereby preparing a negative electrode mixture paste. The negative electrode mixture paste was applied onto both surfaces of a copper foil (collector), dried, processed under pressure and cut into a predetermined size, thereby producing a long rectangular, negative electrode sheet. The density of a part of the negative electrode except the collector was 1.7 g/cm$^3$.

The positive electrode sheet, a porous polyethylene film separator, the negative electrode sheet and a separator were laminated in that order, and the resulting laminate was coiled up. The coil was housed into a nickel-plated, iron-made cylindrical battery can serving also as a negative electrode terminal. Further, the nonaqueous electrolytic solution was injected thereinto, and the can was calked with a battery cap having a positive electrode terminal, via a gasket therebetween, thereby constructing a 18650-type cylindrical battery. The positive electrode terminal was connected to the positive electrode sheet via an aluminium lead tab therebetween; and the negative electrode can was previously connected to the negative electrode sheet inside the battery, via a nickel lead tab therebetween.

(2) Evaluation of Low-Temperature Cycle Property

In a thermostat chamber kept at 25° C., the battery constructed as in the above was charged up to 4.2 V (charging final voltage) with a constant current of 1 C, then charged for 2.5 hours at the constant voltage of 4.2 V, and thereafter this was discharged under a constant current of 1 C to a discharge voltage of 3.0 V (discharging final voltage). Next, in a thermostat chamber kept at 0° C., this was charged up to 4.2 V with a constant current of 1 C, then charged for 2.5 hours at the constant voltage of 4.2 V, and thereafter this was discharged under a constant current of 1 C to a discharge voltage of 3.0 V. This is one cycle. The battery was subjected to 50 cycles.

After 50 cycles at 0° C., the discharge capacity retention rate of the battery was determined according to the following formula, and the results are shown in Table 1.

Discharge Capacity Retention Rate (%) after 50 cycles at 0° C.=(discharge capacity in 50 cycles at 0° C./discharge capacity in 1 cycle at 0° C.)×100.

Examples 5 to 12

Cylindrical batteries were produced in the same manner as in Example 1, for which, however, $LiPF_6$ to be 1 M was dissolved in a nonaqueous solvent of EC/MEC/DMC=30/35/35 (ratio by volume), and further, in place of adding 2,4-difluorophenyl methanesulfonate, 2-fluorophenyl methanesulfonate (Example 5), 3-fluorophenyl methanesulfonate (Example 6), 4-fluorophenyl methanesulfonate (Example 7), 3,4-difluorophenyl methanesulfonate (Example 8), 3,5-difluorophenyl methanesulfonate (Example 9), 2,3,4-trifluorophenyl methanesulfonate (Example 10), 3,4,5-trifluorophenyl methanesulfonate (Example 11) or 2,3,5,6-tetrafluorophenyl methanesulfonate (Example 12) was added thereto to prepare a nonaqueous electrolytic solution, in an amount of 1% by mass of the resulting nonaqueous electrolytic solution; and the batteries were evaluated. The results are shown in Table 1.

Example 13

A cylindrical battery was produced in the same manner as in Example 1, for which, however, $LiPF_6$ to be 1 M was dissolved in a nonaqueous solvent of EC/MEC/DMC=30/35/35 (ratio by volume), and further, 1% by mass of 2,4-difluorophenyl methanesulfonate and 2% by mass of 1,3-propanesultone, relative to the resulting nonaqueous electrolytic solution, were added thereto to prepare a nonaqueous electrolytic solution, and the battery was evaluated. The result is shown in Table 1.

Example 14

A cylindrical battery was produced in the same manner as in Example 1, for which, however, $LiPF_6$ to be 1 M was dissolved in a nonaqueous solvent of EC/MEC/DMC=30/35/35 (ratio by volume), and further, 1% by mass of 2,4-difluorophenyl methanesulfonate and 0.5% by mass of ethylene sulfite, relative to the resulting nonaqueous electrolytic solution, were added thereto to prepare a nonaqueous electrolytic solution, and the battery was evaluated. The result is shown in Table 1.

Example 15

A cylindrical battery was produced in the same manner as in Example 1, for which, however, LiPF$_6$ to be 0.95 M and LiN(SO$_2$CF$_3$)$_2$ to be 0.05 M were dissolved in a nonaqueous solvent of EC/VC/MEC/DEC=28/2/35/35 (ratio by volume), and further, 1% by mass of 2,4-difluorophenyl methanesulfonate and 0.5% by mass of divinyl sulfone, relative to the resulting nonaqueous electrolytic solution, were added thereto to prepare a nonaqueous electrolytic solution, and the battery was evaluated. The result is shown in Table 1.

Example 16

A cylindrical battery was produced in the same manner as in Example 1, for which, however, LiPF$_6$ to be 0.95 M and LiBF$_4$ to be 0.05 M were dissolved in a nonaqueous solvent of FEC/PC/DMC/DEC=20/10/35/35 (ratio by volume), and further, 1% by mass of 2,4-difluorophenyl methanesulfonate, relative to the resulting nonaqueous electrolytic solution, was added thereto to prepare a nonaqueous electrolytic solution, and the battery was evaluated. The result is shown in Table 1.

Comparative Example 1

A cylindrical battery was produced in the same manner as in Example 1, for which, however, LiPF$_6$ to be 1 M was dissolved in a nonaqueous solvent of EC/MEC/DMC=30/35/35 (ratio by volume), but 2,4-difluorophenyl methanesulfonate was not added thereto to prepare a nonaqueous electrolytic solution, and the battery was evaluated. The result is shown in Table 1.

Comparative Examples 2 to 4

Cylindrical batteries were produced in the same manner as in Example 1, for which, however, LiPF$_6$ to be 1 M was dissolved in a nonaqueous solvent of EC/MEC/DMC=30/35/35 (ratio by volume), and further, phenyl methanesulfonate (Comparative Example 2), methyl 2,4-difluorobenzenesulfonate (Comparative Example 3), or methyl 2,4-difluorobenzoate (Comparative Example 4) was added thereto, in place of adding 2,4-difluorophenyl methanesulfonate thereto, in an amount of 1% by mass of the resulting nonaqueous electrolytic solution; and the batteries were evaluated. The results are shown in Table 1.

TABLE 1

|  | Composition of Electrolyte Salt Composition of Nonaqueous Electrolytic Solution (ratio by volume of solvents) | Compound | Amount Added *1 (% by mass) | Discharge Capacity Retention Rate after 50 cycles at 0° C. (%) |
| --- | --- | --- | --- | --- |
| Example 1 | 1M LiPF6 EC/MEC/DMC (30/35/35) | 2,4-difluorophenyl methanesulfonate | 0.1 | 79 |
| Example 2 | 1M LiPF6 EC/MEC/DMC (30/35/35) | 2,4-difluorophenyl methanesulfonate | 1 | 89 |
| Example 3 | 1M LiPF6 EC/MEC/DMC (30/35/35) | 2,4-difluorophenyl methanesulfonate | 5 | 86 |
| Example 4 | 1M LiPF6 EC/MEC/DMC (30/35/35) | 2,4-difluorophenyl methanesulfonate | 10 | 83 |
| Example 5 | 1M LiPF6 EC/MEC/DMC (30/35/35) | 2-fluorophenyl methanesulfonate | 1 | 82 |
| Example 6 | 1M LiPF6 EC/MEC/DMC (30/35/35) | 3-fluorophenyl methanesulfonate | 1 | 80 |
| Example 7 | 1M LiPF6 EC/MEC/DMC (30/35/35) | 4-fluorophenyl methanesulfonate | 1 | 83 |
| Example 8 | 1M LiPF6 EC/MEC/DMC (30/35/35) | 3,4-difluorophenyl methanesulfonate | 1 | 87 |
| Example 9 | 1M LiPF6 EC/MEC/DMC (30/35/35) | 3,5-difluorophenyl methanesulfonate | 1 | 84 |
| Example 10 | 1M LiPF6 EC/MEC/DMC (30/35/35) | 2,3,4-trifluorophenyl methanesulfonate | 1 | 77 |
| Example 11 | 1M LiPF6 EC/MEC/DMC (30/35/35) | 3,4,5-trifluorophenyl methanesulfonate | 1 | 74 |
| Example 12 | 1M LiPF6 EC/MEC/DMC (30/35/35) | 2,3,5,6-tetrafluorophenyl methanesulfonate | 1 | 72 |
| Example 13 | 1M LiPF6 EC/MEC/DMC (30/35/35) + 1,3-propanesultone: 2% | 2,4-difluorophenyl methanesulfonate | 1 | 87 |
| Example 14 | 1M LiPF6 EC/MEC/DMC(30/35/35) + ethylene sulfite: 0.5% | 2,4-difluorophenyl methanesulfonate | 1 | 89 |
| Example 15 | 0.95M LiPF6 + 0.05M LiN(SO2CF3)2 EC/VC/MEC/DEC(28/2/35/35) + divinyl sulfone: 0.5% | 2,4-difluorophenyl methanesulfonate | 1 | 85 |
| Example 16 | 0.95M LiPF6 + 0.05M LiBF4 FEC/PC/DMC/DEC (20/10/35/35) | 2,4-difluorophenyl methanesulfonate | 1 | 86 |
| Comparative Example 1 | 1M LiPF6 EC/MEC/DMC (30/35/35) | none | — | 69 |
| Comparative Example 2 | 1M LiPF6 EC/MEC/DMC (30/35/35) | phenyl methanesulfonate | 1 | 65 |
| Comparative Example 3 | 1M LiPF6 EC/MEC/DMC (30/35/35) | methyl 2,4-difluorobenzenesulfonate | 1 | 64 |

TABLE 1-continued

| | Composition of Electrolyte Salt Composition of Nonaqueous Electrolytic Solution (ratio by volume of solvents) | Compound | Amount Added *1 (% by mass) | Discharge Capacity Retention Rate after 50 cycles at 0° C. (%) |
|---|---|---|---|---|
| Comparative Example 4 | 1M LiPF6 EC/MEC/DMC (30/35/35) | methyl 2,4-difluorobenzoate | 1 | 67 |

*1: Content in nonaqueous electrolytic solution (% by mass)

As in Table 1, the lithium secondary batteries of Examples 1 to 16 have improved low-temperature cycle property, as compared with the lithium secondary battery in Comparative Example 1 in which the phenyl sulfonate compound of the present invention was not added, that in Comparative Example 2 in which phenyl methanesulfonate with no fluorine atom on the benzene ring was added, that in Comparative Example 3 in which methyl 2,4-difluorobenzenesulfonate containing two fluorine atoms on the benzene ring and having the sulfonate ester group directly bonding to the benzene ring via the sulfur atom was added, and that in Comparative Example 4 in which methyl 2,4-difluorobenzoate containing two fluorine atoms on the benzene ring and having the ester group directly bonding to the benzene ring via the carbon atom. Accordingly, it is known that adding a phenyl sulfonate compound of the general formula (II) to a nonaqueous electrolytic solution of an electrolyte salt dissolved in a nonaqueous solvent brings about the unexpected specific effect.

FIG. 1 shows the relationship between the number of fluorine atoms on the benzene ring and the low-temperature cycle property. When the number of the fluorine atoms is one or two, the low-temperature cycle property is especially good; and with the increase in the number of the fluorine atoms more than two, the low-temperature cycle property tended to gradually worsen. Accordingly, the number of the fluorine atoms on the benzene ring is preferably from 1 to 4.

Example 17

A positive electrode sheet was produced, using LiFePO$_4$ (positive electrode active material) in place of the positive electrode active material used in Example 2. 90% by mass of LiFePO$_4$ and 5% by mass of acetylene black (electroconductive agent) were mixed, and added to and mixed with a solution previously prepared by dissolving 5% by mass of polyvinylidene fluoride (binder) in 1-methyl-2-pyrrolidone, thereby preparing a positive electrode mixture paste. A cylindrical battery was produced and evaluated in the same manner as in Example 2, for which, however, the positive electrode mixture paste was applied onto an aluminium foil (collector), dried, processed under pressure and cut into a predetermined size, thereby producing a long rectangular, positive electrode sheet, and the final charging voltage was 3.6 V and the final discharging voltage was 2.0 V. The result is shown in Table 2.

Comparative Example 5

A cylindrical battery was produced in the same manner as in Example 17, for which, however, 2,4-difluorophenyl methanesulfonate was not added to the nonaqueous electrolytic solution; and the battery was evaluated. The result is shown in Table 2.

Example 18

A negative electrode sheet was produced, using Si (negative electrode active material) in place of the negative electrode active material used in Example 1. 80% by mass of Si and 15% by mass of acetylene black (electroconductive agent) were mixed, and added to and mixed with a solution previously prepared by dissolving 5% by mass of polyvinylidene fluoride (binder) in 1-methyl-2-pyrrolidone, thereby preparing a negative electrode mixture paste. A cylindrical battery was produced in the same manner as in Example 2, for which, however, the negative electrode mixture paste was applied onto a copper foil (collector), dried, processed under pressure and cut into a predetermined size, thereby producing a long rectangular, negative electrode sheet; and the battery was evaluated. The result is shown Table 2.

Comparative Example 6

A cylindrical battery was produced in the same manner as in Example 18, for which, however, 2,4-difluorophenyl methanesulfonate was not added to the nonaqueous electrolytic solution; and the battery was evaluated. The result is shown Table 2.

TABLE 2

| | Composition of Electrolyte Salt Composition of Nonaqueous Electrolytic Solution (ratio by volume of solvents) | Compound | Amount Added *1 (% by mass) | Discharge Capacity Retention Rate after 50 cycles at 0° C. (%) |
|---|---|---|---|---|
| Example 17 | 1M LiPF6 EC/MEC/DMC (30/35/35) | 2,4-difluorophenyl methanesulfonate | 1 | 85 |
| Comparative Example 5 | 1M LiPF6 EC/MEC/DMC (30/35/35) | none | 1 | 65 |
| Example 18 | 1M LiPF6 EC/MEC/DMC (30/35/35) | 2,4-difluorophenyl methanesulfonate | 1 | 71 |
| Comparative Example 6 | 1M LiPF6 EC/MEC/DMC (30/35/35) | none | 1 | 54 |

*1: Content in nonaqueous electrolytic solution (% by mass)

In Table 2, from comparison between Example 17 and Comparative Example 5 and comparison between Example 18 and Comparative Example 6, it is known that adding a phenyl sulfonate compound of the general formula (II) to the case of using a lithium-containing olivine-type iron phosphate for the positive electrode and to the case of using Si for the negative electrode also brings about the unexpected specific effect. Accordingly, it is obvious that the effect of the present invention does not depend on a specific positive electrode or negative electrode.

Further, the nonaqueous electrolytic solution of the present invention has the effect of improving the low-temperature discharge property of lithium primary batteries.

INDUSTRIAL APPLICABILITY

According to the present invention, there is provided a novel phenyl sulfonate compound useful as intermediate materials for medicines, agricultural chemicals, electronic materials, polymer materials and the like, or as battery materials. Using the nonaqueous electrolytic solution containing the phenyl sulfonate compound of the present invention brings about lithium batteries excellent in low-temperature cycle property.

The invention claimed is:

1. A phenyl sulfonate compound of formula (I):

[Formula 1]

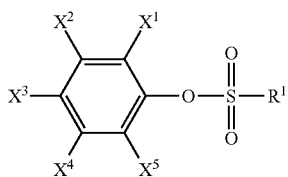

(I)

wherein:
X$^1$, X$^2$, X$^3$, X$^4$, and X$^5$ are each independently a fluorine atom or a hydrogen atom, wherein two of these are fluorine atoms and three of these are hydrogen atoms; and
R$^1$ is a linear or branched alkyl group comprising from 1 to 6 carbon atoms, a linear or branched alkyl group comprising from 1 to 6 carbon atoms in which at least one hydrogen atom is substituted with a halogen atom, or an aryl group comprising from 6 to 9 carbon atoms.

2. The phenyl sulfonate compound of claim 1, wherein R$^1$ is a methyl group, an ethyl group, a trifluoromethyl group, or a phenyl group.

3. The phenyl sulfonate compound of claim 2, wherein R$^1$ is a methyl group.

4. The phenyl sulfonate compound of claim 3, wherein the phenyl sulfonate is 2,3-difluorophenyl methanesulfonate, 2,4-difluorophenyl methanesulfonate, 2,5-difluorophenyl methanesulfonate, 2,6-difluorophenyl methanesulfonate, 3,4-difluorophenyl methanesulfonate, 3,5-difluorophenyl methanesulfonate, or any combination thereof.

5. A nonaqueous electrolytic solution, comprising:
an electrolyte salt dissolved in a nonaqueous solvent; and
from 0.01 to 10% by mass, based on the mass of the nonaqueous electrolytic solution, of a phenyl sulfonate compound of formula (II):

[Formula 2]

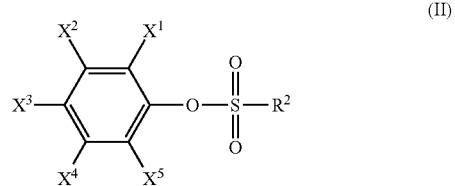

(II)

wherein:
X$^1$, X$^2$, X$^3$, X$^4$, and X$^5$ are each independently a fluorine atom or a hydrogen atom, wherein one or two of these are fluorine atoms and three or four of these are hydrogen atoms; and
R$^2$ is a linear or branched alkyl group comprising from 1 to 6 carbon atoms, a linear or branched alkyl group comprising from 1 to 6 carbon atoms in which at least one hydrogen atom is substituted with a halogen atom, or an aryl group comprising from 6 to 9 carbon atoms.

6. A lithium battery, comprising:
a positive electrode;
a negative electrode; and
the nonaqueous electrolytic solution of claim 5.

7. The nonaqueous electrolytic solution of claim 5, wherein R$^2$ is a methyl group, an ethyl group, a trifluoromethyl group, or a phenyl group.

8. The nonaqueous electrolytic solution of claim 7, wherein R$^2$ is a methyl group.

9. The nonaqueous electrolytic solution of claim 8, wherein the phenyl sulfonate compound is 2-fluorophenyl methanesulfonate, 3-fluorophenyl methanesulfonate, 4-fluorophenyl methanesulfonate, 2,3-difluorophenyl methanesulfonate, 2,4-difluorophenyl methanesulfonate, 2,5-difluorophenyl methanesulfonate, 2,6-difluorophenyl methanesulfonate, 3,4-difluorophenyl methanesulfonate, 3,5-difluorophenyl methanesulfonate, or any combination thereof.

10. The nonaqueous electrolytic solution of claim 5, wherein, in formula (II), two of X$^1$ to X$^5$ are fluorine atoms and three of X$^1$ to X$^5$ are hydrogen atoms.

11. The nonaqueous electrolytic solution of claim 5, wherein the nonaqueous solvent is ethylene carbonate, propylene carbonate, butylene carbonate, 4-fluoro-1,3-dioxolan-2-one, trans or cis-4,5-difluoro-1,3-dioxolan-2-one, vinylene carbonate, vinylethylene carbonate, or any combination thereof.

12. The nonaqueous electrolytic solution of claim 5, wherein the nonaqueous solvent comprises a cyclic carbonate in a content of from 10% to 40% by volume.

13. The nonaqueous electrolytic solution of claim 5, wherein the nonaqueous solvent comprises a linear carbonate in a content of from 60% to 90% by volume.

14. The nonaqueous electrolytic solution of claim 5, wherein the electrolyte salt comprises lithium.

15. The nonaqueous electrolytic solution of claim 14, wherein the electrolyte salt comprises LiPF$_6$ and at least one second salt selected from the group consisting of LiBF$_4$, LiN(SO$_2$CF$_3$)$_2$, and LiN(SO$_2$C$_2$F$_5$)$_2$.

16. The nonaqueous electrolytic solution of claim 15, wherein a molar ratio of LiPF$_6$ to the at least one second salt is from 70/30 to 99/1.

17. The nonaqueous electrolytic solution of claim 16, wherein a molar ratio of LiPF$_6$ to the at least one second salt is from 80/20 to 98/2.

18. The nonaqueous electrolytic solution of claim 15, wherein a content of the at least one second salt is from 0.01 to 45 mol % of a total of electrolyte salts in the solution.

19. The nonaqueous electrolytic solution of claim 5, wherein the nonaqueous solvent comprises a cyclic carbonate and a linear carbonate.

20. The nonaqueous electrolytic solution of claim 19, wherein the cyclic carbonate is ethylene carbonate, propylene carbonate, butylene carbonate, 4-fluoro-1,3-dioxolan-2-one, trans or cis-4,5-difluoro-1,3-dioxolan-2-one, vinylene carbonate, vinylethylene carbonate, or any combination thereof.

21. The nonaqueous electrolytic solution of claim 19, wherein the linear carbonate is methyl ethyl carbonate, methyl propyl carbonate, methyl isopropyl carbonate, methyl butyl carbonate, ethyl propyl carbonate, or any combination thereof.

22. The nonaqueous electrolytic solution of claim 2, wherein the electrolyte salt is $LiPF_6$, $LiBF_4$, $LiN(SO_2CF_3)_2$, $LiN(SO_2C_2F_5)_2$, or any combination thereof.

23. The nonaqueous electrolytic solution of claim 22, wherein the electrolyte salt is $LiPF_6$.

24. The nonaqueous electrolytic solution of claim 19, wherein the cyclic carbonate is ethylene carbonate and the linear carbonate is methyl ethyl carbonate.

25. The nonaqueous electrolytic solution of claim 24, wherein the nonaqueous solvent comprises the ethylene carbonate in a content of from 10% to 40% by volume and the methyl ethyl carbonate in a content of from 60% to 90% by volume.

* * * * *

UNITED STATES PATENT AND TRADEMARK OFFICE
CERTIFICATE OF CORRECTION

PATENT NO. : 8,512,897 B2  Page 1 of 1
APPLICATION NO. : 12/740122
DATED : August 20, 2013
INVENTOR(S) : Abe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 558 days.

Signed and Sealed this

Fifteenth Day of September, 2015

Michelle K. Lee
*Director of the United States Patent and Trademark Office*